United States Patent
Ludwig et al.

(10) Patent No.: US 8,363,050 B2
(45) Date of Patent: Jan. 29, 2013

(54) METHOD AND DEVICE FOR PRODUCING A TOMOSYNTHETIC 3D X-RAY IMAGE

(75) Inventors: Jasmina Ludwig, Erlangen (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 805 days.

(21) Appl. No.: 12/300,404

(22) PCT Filed: Feb. 8, 2007

(86) PCT No.: PCT/EP2007/051200
§ 371 (c)(1),
(2), (4) Date: May 13, 2009

(87) PCT Pub. No.: WO2007/134882
PCT Pub. Date: Nov. 29, 2007

(65) Prior Publication Data
US 2010/0007659 A1   Jan. 14, 2010

(30) Foreign Application Priority Data
May 24, 2006   (DE) .................... 10 2006 024 413

(51) Int. Cl.
*G06T 15/00* (2011.01)
(52) U.S. Cl. ................ 345/419; 345/427; 378/2; 378/4; 378/9; 378/14; 378/19; 378/21; 378/22; 378/23; 378/37; 378/197; 378/901; 382/131; 600/427
(58) Field of Classification Search .................. 345/419, 345/427; 378/2, 4, 9, 14, 19, 21, 22, 23, 378/37, 197, 901; 382/131; 600/427
See application file for complete search history.

(56) References Cited

U.S. PATENT DOCUMENTS

| | | | |
|---|---|---|---|
| 4,566,112 A | 1/1986 | Linde et al. | |
| 5,060,246 A | 10/1991 | Van Der Brug et al. | |
| 5,668,844 A | 9/1997 | Webber | |
| 5,872,828 A | 2/1999 | Niklason et al. | |
| 6,292,531 B1 * | 9/2001 | Hsieh | 378/37 |
| 6,960,020 B2 | 11/2005 | Lai | |
| 7,274,766 B2 * | 9/2007 | Kaipio et al. | 378/22 |
| 7,444,011 B2 | 10/2008 | Pan et al. | |
| 7,653,229 B2 * | 1/2010 | Kaufhold et al. | 382/131 |
| 7,831,296 B2 * | 11/2010 | DeFreitas et al. | 600/427 |
| 2005/0226375 A1 * | 10/2005 | Eberhard et al. | 378/62 |
| 2011/0069808 A1 * | 3/2011 | DeFreitas et al. | 378/5 |

OTHER PUBLICATIONS

Tao Wu et al. "Tomographic mamography using a limited number of low-dose cone-beam projection images". Published 2003.*

* cited by examiner

Primary Examiner — Kimbinh T Nguyen
(74) Attorney, Agent, or Firm — Schiff Hardin LLP

(57) ABSTRACT

In a method and device for generating a tomosynthetic 3D x-ray image, a number of digital x-ray images of an examination subject are acquired at respectively different projection angles, within a limited angle range, using an x-ray source and a digital x-ray detector. At an initial position for a selected projection angle, a spatially-fixed reference point is projected onto a partial region of the acquisition surface of the x-ray detector. For each further projection angle, a corresponding partial region on the acquisition surface is automatically determined. The tomosynthetic 3D image is reconstruction exclusively using image data from the respective partial regions.

9 Claims, 2 Drawing Sheets

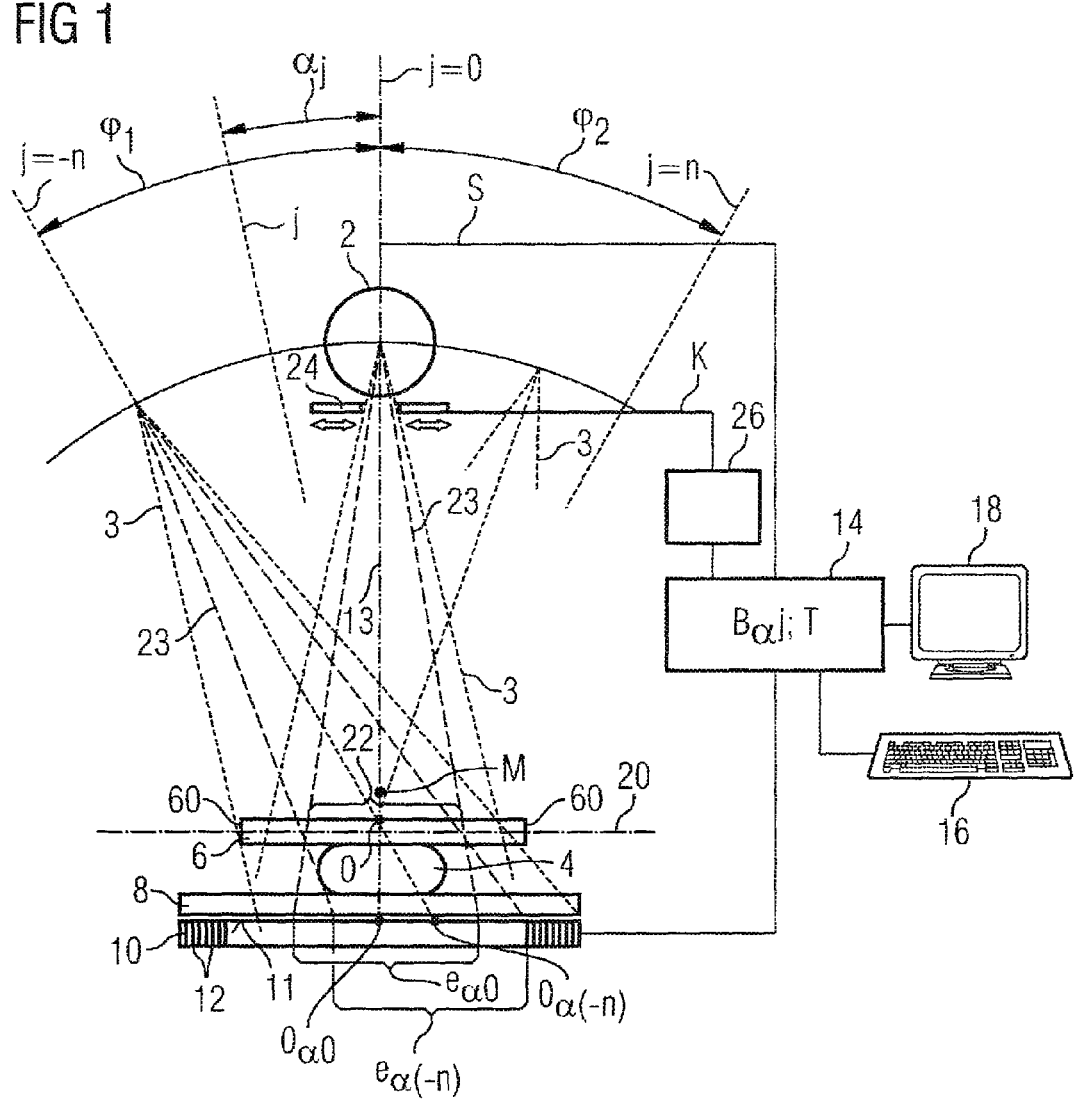

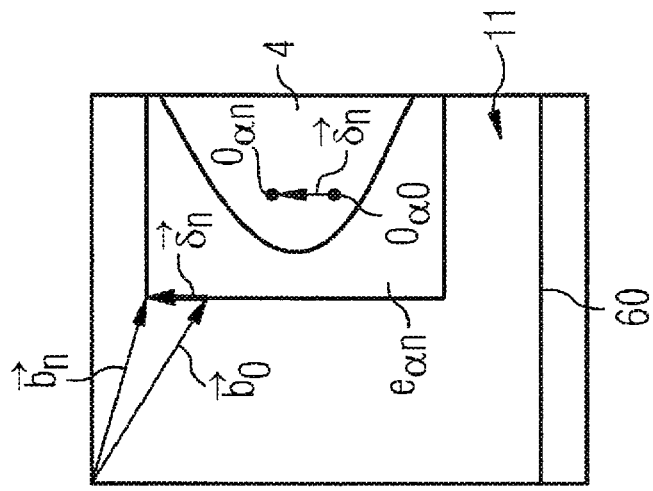
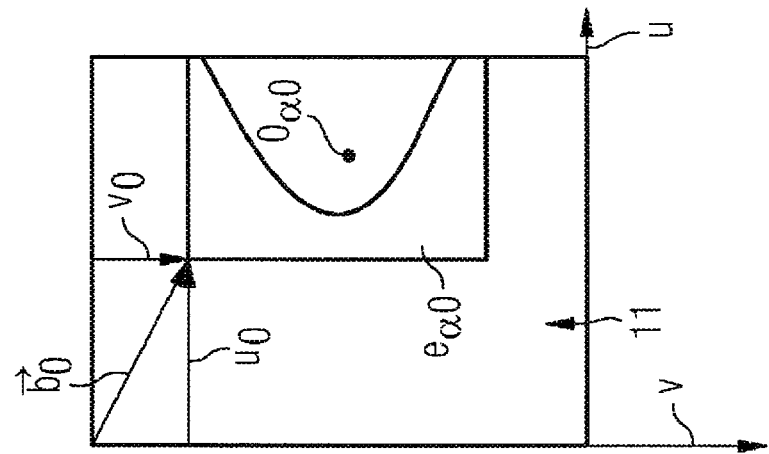
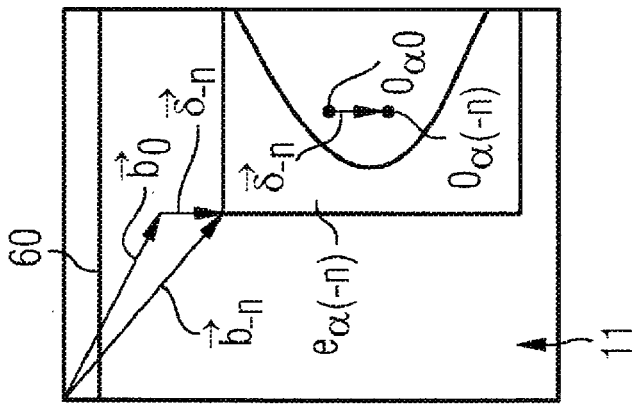

METHOD AND DEVICE FOR PRODUCING A TOMOSYNTHETIC 3D X-RAY IMAGE

FIELD OF THE INVENTION

The present invention concerns a method, suitable in particular for mammography, for generation of tomosynthetic x-ray image of an examination subject in which a tomosynthetic 3D x-ray image is assembled from a number of digital single images acquired with varying projection angles. The invention also concerns a device operable with such a method.

DESCRIPTION OF THE PRIOR ART

Mammography is an x-ray examination of the female breast, with the goal of detecting tumors at as early a stage as possible. Through continual improvement of mammography techniques, it is sought to generate x-ray images with high clarity in order to differentiate benign from malignant variations and to reduce the number of incorrect findings (i.e. the number of suspect findings that are caused by non-malignant variations) and the number of the undetected malignant tumors. In conventional x-ray mammography, a two-dimensional single image of the compressed breast is generated in a single projection direction. Since the successive tissue layers are overlapping in the direction of the x-ray beam in such a projection, strongly absorbing benign structures can overlap a malignant tumor and hinder the ability to detect it, or in a disadvantageous case a malignant tumor can be simulated by superimposition of tissue structures.

In order to prevent such diagnostic problems, mammography methods (designated as tomosynthesis, in which single images of the female breast or projection data are acquired in a number of different projection directions with a digital x-ray detector) are known, for example from Dobbis J T III, Godfrey D J, "Digital x-ray tomosynthesis: current state of the art and clinical potential", Physics in Medicine and Biology 48, R65-R106, 2003. A three-dimensional image data set that, for example, is composed of a number of slice images that respectively reproduce a slice of the breast oriented parallel to the acquisition surface of the x-ray detector can then be generated by image reconstruction methods from these digital single images acquired from varying projection angles (i.e. from the image data belonging to these single images). Such an image data set acquired by reconstruction is designated in the following as a tomosynthetic 3D x-ray image. Deeper (in the propagation direction of the x-ray beam) tissue structures can be better detected by the generation of such a tomosynthetic 3D x-ray image.

However, the examination subject to be acquired normally occupies only a portion of the acquisition area of the x-ray detector, such that a portion of the image data provided by the x-ray detector is irrelevant to the tomosynthetic image reconstruction and only leads to an increase of the time and calculation requirement for the reconstruction of the tomosynthetic 3D x-ray image.

SUMMARY OF THE INVENTION

An object of the present invention is to provide a method for generation of a tomosynthetic 3D x-ray image in which the calculation and time cost for the reconstruction of the tomosynthetic 3D x-ray image is reduced without loss of image quality. A further object of the invention is to provide a device suitable for implementation of the method.

With regard to the method, the cited object is achieved with a method for generation of a tomosynthetic 3D x-ray image wherein a number of digital x-ray images of an examination subject are acquired with varying projection angles in a limited angle range with an x-ray source and a digital x-ray detector, and a partial region of an acquisition surface of the x-ray detector is established for an initial position at a selected projection angle, by projecting at least one spatially-fixed reference point, that is established between the x-ray source and the x-ray detector, onto this partial region at the selected projection angle. By projection of this at least one spatially-fixed reference point on the acquisition surface of the x-ray detector at the other projection angles, partial region is determined for each projection angle, and the tomosynthetic 3D x-ray image is calculated exclusively using the image data of the partial regions.

Since only the image data of a partial region of the x-ray detector that is actually relevant for the diagnostic assessment or the medical procedure (for example a biopsy) is used for the tomosynthetic image reconstruction, the calculation and time cost for the reconstruction (for example a filtered back-projection) is significantly reduced, and only the size of the partial reigns selected from diagnostic points of view and limited to the examination subject or, respectively, to a partial area of the examination subject is determined. Moreover, since normally the border regions of an x-ray image utilizing the entire acquisition surface of the x-ray detector lie outside of these partial regions, the quality of the tomosynthetic 3D x-ray image is additionally improved. The border regions namely frequently contain interfering objects (for example an edge of the compression plate in mammography) that disadvantageously influence the image quality in the reconstruction since these lead (in particular in filterings conducted in the framework of the reconstruction) to overshoots that disadvantageously affect the diagnostically relevant regions in the x-ray image that are separated from the interfering object.

Since the partial regions are matched to the respective projection angles, i.e. are entrained with the projection angle, it is possible to select these optimally small since the position of the partial region on the acquisition surface depends on the projection angle at least approximately in the same way as the position of the examination subject or, respectively, the diagnostically relevant partial area of the examination subject.

The at least one reference point lies at least in proximity to the examination subject. Instead of a single reference point or a plurality of reference points, a reference area can also be established that serves as a mask, and its projection on the acquisition surface yields the partial region valid for the respective projection angle.

If the partial regions are equal in area and congruent among one another and their position is defined via projection of a single reference point, the calculation cost for the subsequent tomosynthetic image reconstruction is reduced.

If the at least one reference point lies at the height level of an interfering object, i.e. of an object lying in the beam path of the x-ray beam and generating interference in the image reproduction, given sufficiently small partial regions it can be achieved that the interfering object is not contained in all x-ray images respectively reproducing the partial regions.

Moreover, if the x-ray beam used to generate the single images is collimated depending on the projection angle such that essentially only the respective associated partial region is irradiated, the risk of an overexposure of the x-ray detector in the partial region is reduced. Moreover, the exposed region is limited to the region actually relevant to the diagnostic or medical procedure (for example a biopsy), and an unnecessary dose load in the irrelevant surroundings of the examination subject is reduced. Moreover, a dose load caused by scatter radiation in the surroundings of the x-ray device is also reduced.

In a further embodiment of the method, the determination of the partial region ensues automatically via an image processing method.

The above object also is achieved in accordance with the present invention by a device constructed and configured to implement a method as described above.

BRIEF DESCRIPTION OF THE DRAWINGS

FIG. 1 schematically illustrates an exemplary embodiment of a device constructed and operating in accordance with the present invention.

FIGS. 2A, 2B and 2C respectively illustrate simplified images acquired from different projection angles in the method in accordance with the present invention.

DESCRIPTION OF THE PREFERRED EMBODIMENTS

According to FIG. 1, the device (a mammography apparatus in the exemplary embodiment) comprises an x-ray source 2 (normally an x-ray tube) to generate x-rays 3 that pass through an examination subject 4. The examination subject 4 is a female breast that is embedded between a compression plate 6 and a support plate 8. The x-rays 3 passing through the examination subject 4, the compression plate 6 and the support plate 8 are received by a large-area digital x-ray detector 10 that is made up of a plurality of individual detectors 12 arranged in a matrix-shaped array, the acquisition surface 11 of which x-ray detector 10 being arranged parallel to the compression plate 6 and to the support plate 8.

The x-ray source 2 is mounted so as to be spatially variable relative to the examination subject and can be panned in a limited angle range $\phi_1$, $\phi_2$ (for example on an axis M perpendicular to the plane off the drawing) into different angle positions $j=-n \ldots +n$ so that x-ray images of the examination subject 4 with different projection angles $\alpha_j$ can be generated relative to a middle axis 13 standing perpendicular to the acquisition surface 11. The angle range $\phi_1$, $\phi_2$ thereby does not need to be arranged symmetrical to this middle axis 13. These x-ray images or the projection data $P_{\alpha j}$ respectively associated therewith are assembled into a tomosynthetic 3D x-ray image T and presented on a monitor 18 in a control and evaluation device 14 containing an image computer.

In the exemplary embodiment, the x-ray detector 10 is stationary during the panning movement of the x-ray source 2. However, in principle it is also possible to pan the x-ray detector 10 together with the x-ray source 2, or to linearly displace the x-ray detector 10 following the panning movement of the x-ray source 2.

A movement of the x-ray source 2 on a limited, linear track instead of the panning is permissible, such that the height difference between x-ray detector 10 and x-ray tube remains constant. This linear track does not necessarily need to likewise proceed symmetrical to the middle axis 13. Given this linear movement, an alignment of the x-ray source 2 on the examination subject 4 ensues so that even in this case single images of the examination subject 4 can be acquired from varying projection angles $\alpha_j$ in a limited angle range.

The control of the angle position j—or, in the case of a linear displacement, of the linear position—and of the alignment of the x-ray source 2 as well as its operating parameters ensues via control signals S that are generated by the control and evaluation device 14.

With the use of input elements (symbolically illustrated by a keyboard 16 in the example), a partial region $e_{\alpha 0}$ of the acquisition surface 1 of the x-ray detector 10 is now selected by the user in an angle position j selected by him (in the exemplary embodiment the angle position $j=0$ belonging to the projection angle 0°), which partial region $e_{\alpha 0}$ is classified by the user as relevant to the diagnostic assessment (ROI, region of interest). A stationary reference point O that is positioned such that its projection point $O_{\alpha 0}$ lies within the partial region $e_{\alpha 0}$ on the acquisition surface 11 is now established between x-ray detector 10 and x-ray source 2. In the exemplary embodiment of FIG. 1, the reference point O is located within the compression plate 6, and therefore at the height level of an object (the edges of the compression plate 6 in the case of the example, i.e. a mechanically stable, height-adjustable retention frame with which the compression plate 6 is fixed) situated in the beam path of the x-rays 3 and interfering with the x-ray image.

As an alternative, the selection of the partial region $e_{\alpha 0}$ can ensue automatically with an image processing method (for example via a segmentation method) with which a subject (the breast in the example) in the image is detected and its spatial boundaries are established. In this case the reference point O is automatically placed at a point at the level of the compression plate 6 in which a vertical line emanating from the acquisition surface 11 intersects the compression plate 6 from the image center of the subject detected by image segmentation.

With the use of the projections (belonging to the various angle positions j) of the spatially determined reference point O on the acquisition surface 11 of the x-ray detector 10, a partial region $e_{\alpha j}$ is now determined for each angle position j, in that the partial region $e_{\alpha 0}$ established in the selected angle position $j=0$ is linearly displaced by the vector between the projection point $O_{\alpha 0}$ arising at the selected angle position $j=0$ via projection of the reference point O and the projection point $O_{\alpha j}$ arising at the angle position j via projection of the reference point O. This is shown in FIG. 2 using the angle position $j=-n$, for example $-25°$. From FIG. 1 it can be seen that in this way a laterally displaced partial region $e_{\alpha(-n)}$ arises at the angle position $j=-n$ that is congruent with and equal in size to the established partial region $e_{\alpha 0}$. Moreover, it can be seen that an edge 60 of the compression plate 6 (in the drawing the left edge 60) is depicted at the angle position $j=-n$ given utilization of the entire acquisition surface 11.

The calculation of the position of the projection point $O_{\alpha j}$ ensues with the aid of projection matrices $P_j$ according to a method explained in detail in, for example, DE 198 19 519 B4 or in IEEE Transactions on Medical Imaging, Vol. 19, No. 5, May 2000, P. 391-403.

However, in principle the partial regions $e_{\alpha j}$ belonging to various angle positions can also be established in that they are identical with an area that corresponds to the projection of an area 22 on the acquisition surface 11 that is arranged in a plane 20 between x-ray detector 10 and x-ray source 2 and serves as a mask. However, this would mean that the partial regions $e_{\alpha j}$ would vary both in their size and in their shape depending on the angle position j. In order to reduce the calculation burden in the tomosynthetic reconstruction, it is advantageous—as explained above—to project only a selected reference point O onto the acquisition surface 11 and, starting from the projection point $O_{\alpha j}$ formed in this way, to respectively establish partial regions $e_{\alpha 0}$ of equal size and shape that can be brought into congruence among one another via a simple linear displacement.

For the tomosynthetic image reconstruction, exclusively the image or projection data $B_{\alpha j}$ of the partial regions $e_{\alpha j}$ (partial images) are now respectively evaluated in the evaluation device 14.

After establishing the spatially fixed reference point O as well as the partial region $e_{\alpha 0}$, and therefore after establishing a partial beam 23 of the x-ray beam 3 that is actually used for image generation, this x-ray beam 3 can be limited to the actually required partial beam 23 with the aid of a collimator 24 arranged in front of the x-ray source 2 (illustrated in the example of FIG. 1 by an adjustable diaphragm). The adjustment of the collimator 24 ensues automatically depending on the angle position j, with the aid of control signals K that are provided by a control device 26 depending on the angle position j and the reference point O established by the user as well as the partial region $e_{\alpha 0}$ established by him at the starting position.

It can be seen in FIGS. 2A, 2B and 3C (which respectively illustrate x-ray images acquired at different angle positions j=−n, j=0 and j=+n) that the examination subject 4 is imaged in different regions of the acquisition surface 11 of the x-ray detector, depending on the angle position j. What is now shown is respectively a complete image that is created when the entire acquisition surface 11 of the x-ray detector is used, as well as an (in the example rectangular) partial region $e_{\alpha(-n)}$, $e_{\alpha 0}$, $e_{\alpha n}$ of the acquisition surface 11 as established according to the invention.

In FIGS. 2A through 2C it can be seen that an edge 60 of the compression plate is respectively projected onto the acquisition surface 11 of the x-ray detector at extreme angle positions j=−n, +n. FIGS. 2A through 2C now show that the partial regions $e_{\alpha(-n)}$, $e_{\alpha n}$ (congruent rectangles in the shown example) arise via linear displacement by the vectors $\vec{\delta}_{-n} = \overrightarrow{O_{\alpha 0} O_{\alpha(-n)}}$ and $\vec{\delta}_n = \overrightarrow{O_{\alpha 0} O_{\alpha n}}$ from the partial region $e_{\alpha 0}$. The position of the pixel of the upper left image border of each partial region $e_{\alpha j}$ in the coordinate system of the acquisition surface 11 is then provided by a linear displacement by the vector $\vec{b_O} + \vec{\delta}_j = (u_j, v_j)$, wherein the vector $\vec{b_O} = (u_O, v_O)$ indicates the position of the upper left pixel in the established partial region $e_{\alpha 0}$. Moreover, in FIGS. 1 and 2A-2C it can be seen that the position of the examination subject 4 in the partial regions $e_{\alpha j}$ also varies due to the selection of a reference point O located outside of the examination subject 4.

If the image data of the respective partial regions are presented in a coordinate system dependent on the projection angle $\alpha_j$, in which coordinate system the left upper image border is simultaneously the origin (0, 0), the projection matrix $P'_j$ necessary for the implementation of the back-projection results from the projection matrix $P_j$ based on the detector coordinate system by the relationship $$P'_j = \begin{pmatrix} 1 & 0 & -u_j \\ 0 & 1 & -v_j \\ 0 & 0 & 1 \end{pmatrix} P_1 \text{ with } \vec{\delta}_j = (u_j, v_j).$$

Although modifications and changes may be suggested by those skilled in the art, it is the intention of the inventors to embody within the patent warranted heron all changes and modifications as reasonably and properly come within the scope of their contribution to the art.

We claim as our invention:

1. A method for generating a tomosynthetic 3D x-ray image, comprising the steps of:

acquiring a plurality of digital 2D x-ray images of an examination subject respectively from different projection angles within a limited angle range using an x-ray source and a digital x-ray detector having an acquisition surface;

in an initial position of the x-ray source at a selected projection angle, projecting at least one spatially-fixed reference point, that is between said x-ray source and said x-ray detector, onto a partial region of the acquisition surface of the x-ray detector; and setting said at least one spatially-fixed reference point to be at a height above said examination subject that reduces irradiation of said acquisition surface by x-rays from said x-ray source that are not attenuated by said examination subject;

providing the projection of said at least one spatially fixed reference point onto said partial region of said acquisition surface at the projection angle for said initial position to a computer and, in said computer, using the projection of said at least one spatially fixed reference point provided thereto to automatically determine, for each further projection angle, a partial region of said acquisition surface that contains a projection of said at least one spatially fixed reference point onto said acquisition surface, thereby obtaining a plurality of partial regions respectively for a plurality of projection angles; and after irradiating the examination subject at each of said plurality of projection angles, generating a tomosynthetic 3D x-ray image in said computer using exclusively image data from said plurality of partial regions and making said tomosynthetic 3D x-ray image available as a data file at an output of said computer.

2. A method as claimed in claim 1 comprising automatically determining said plurality of partial regions with all of said partial regions being equal in area and congruent with each other, as defined by respective projections of said single reference point on said acquisition surface of said x-ray detector.

3. A method as claimed in claim 1 comprising employing said at least one spatially fixed reference point at a height level above said acquisition surface corresponding to a height level of a physical object, other than said subject, between said x-ray source and said x-ray detector.

4. A method as claimed in claim 1 comprising collimating an x-ray beam from said x-ray source used to generate said image data dependent on the respective projection angles, so that only said partial region is irradiated at each of said projection angles.

5. A method as claimed in claim 1 comprising automatically establishing said partial regions using an image processing algorithm.

6. A device for generating a tomosynthetic 3D x-ray image, comprising:

an imaging system comprising an x-ray source and a digital x-ray detector having an acquisition surface, said imaging system being configured to acquire a plurality of digital 2D x-ray images of an examination subject respectively from different projection angles within a limited angle range using an x-ray source and a digital x-ray detector;

said imaging system being configured, in an initial position of the x-ray source at a selected projection angle, to project at least one spatially-fixed reference point, that is between said x-ray source and said x-ray detector, onto a partial region of the acquisition surface of the x-ray detector, with said at least one spatially-fixed reference point set to be at a height above said examination subject that reduces irradiation of said acquisition surface by x-rays from said x-ray source that are not attenuated by said examination subject;

a computer supplied with the projection of said at least one spatially fixed reference point onto said partial region of said acquisition surface at the projection angle for said initial position, said computer being configured to use the projection of said at least one spatially fixed reference point supplied thereto to automatically determine, for each further projection angle, a partial region of said acquisition surface that contains a projection of said at least one spatially fixed reference point onto said acquisition surface, thereby obtaining a plurality of partial regions respectively for a plurality of projection angles; and after irradiating the examination subject at each of said plurality of projection angles, said computer being configured to generate a tomosynthetic 3D x-ray image using exclusively image data from said plurality of partial regions, and making said tomosynthetic 3D x-ray image available as a data file at an output of said computer.

7. A device as claimed in claim 6 wherein said imaging system comprises a controllable collimator disposed in a path of an x-ray beam emitted by said x-ray source, and wherein said computer is configured to control operation of said collimator dependent the respective projection angles to cause only the respective partial regions to be irradiated at the respective projection angles.

8. A device as claimed in claim 6 wherein said imaging system comprises a physical object, other than said subject, located between said x-ray source and said x-ray detector, and wherein said reference point is located on said physical object.

9. A device as claimed in claim 8 wherein said imaging system is configured to irradiate a female breast, as said subject and wherein said physical object is a compression plate configured to compress the female breast against said x-ray detector during acquisition of said plurality of digital 2D x-ray images.

* * * * *